(12) United States Patent
Nitz

(10) Patent No.: US 7,221,973 B2
(45) Date of Patent: May 22, 2007

(54) MAGNETIC RESONANCE TOMOGRAPHY METHOD AND APPARATUS WITH MOTION CORRECTION

(75) Inventor: Wolfgang Nitz, Buch (DE)

(73) Assignee: Siemens Aktiengesellschaft, Munich (DE)

( * ) Notice: Subject to any disclaimer, the term of this patent is extended or adjusted under 35 U.S.C. 154(b) by 1219 days.

(21) Appl. No.: 10/119,171

(22) Filed: Apr. 9, 2002

(65) Prior Publication Data

US 2003/0023154 A1   Jan. 30, 2003

(30) Foreign Application Priority Data

Apr. 9, 2001   (DE) ............................... 101 17 752

(51) Int. Cl.
*A61B 5/055* (2006.01)

(52) U.S. Cl. .................. 600/410; 600/411; 600/413; 600/419; 600/420; 600/534

(58) Field of Classification Search ............... 600/410, 600/411, 413, 419, 420, 424; 324/306, 307, 324/309

See application file for complete search history.

(56) References Cited

U.S. PATENT DOCUMENTS

| 5,427,101 | A | | 6/1995 | Sachs et al. |
| 5,792,056 | A | | 8/1998 | Prince |
| 6,073,041 | A | * | 6/2000 | Hu et al. .................... 600/410 |
| 6,268,730 | B1 | * | 7/2001 | Du ............................. 324/309 |

* cited by examiner

*Primary Examiner*—Ruth S. Smith
(74) *Attorney, Agent, or Firm*—Schiff Hardin LLP

(57) ABSTRACT

In a magnetic resonance tomography apparatus and method with motion correction in an angiography examination with magnetic resonance-monitored vessel intervention, a contrast agent-supported exposure of the vessel system (road map) is registered, with one exposure ensuing at the end of expiration and one exposure ensuing at the end of inspiration of the patient, and a magnetic resonance-visible medical intervention device introduced into the vessel system also is registered. A corrected road map of the vessel system is interpolated from the exposures at the end of inspiration and the end of expiration and the exposure of the intervention device is superimposed on the corrected road map.

26 Claims, 2 Drawing Sheets

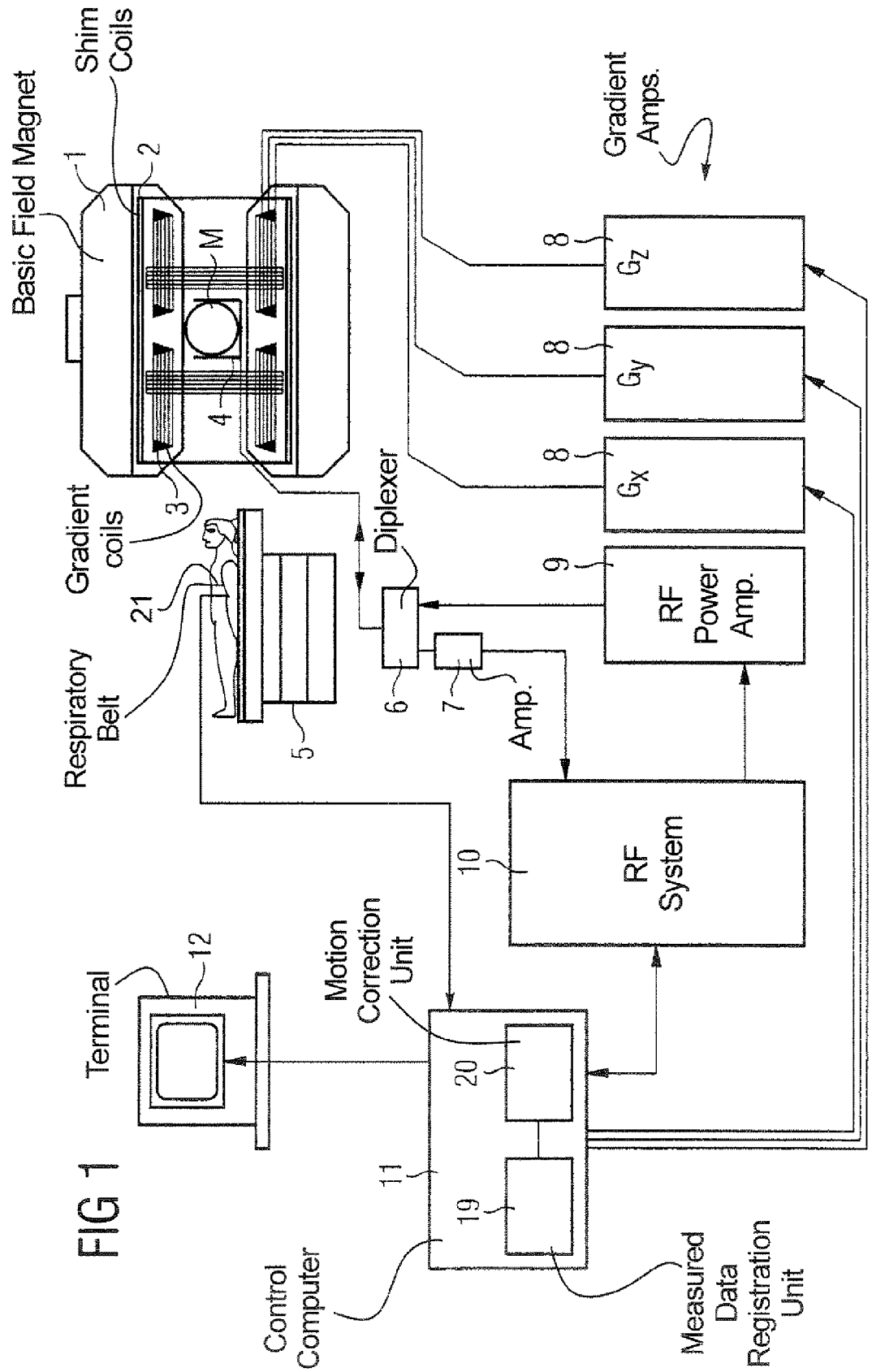

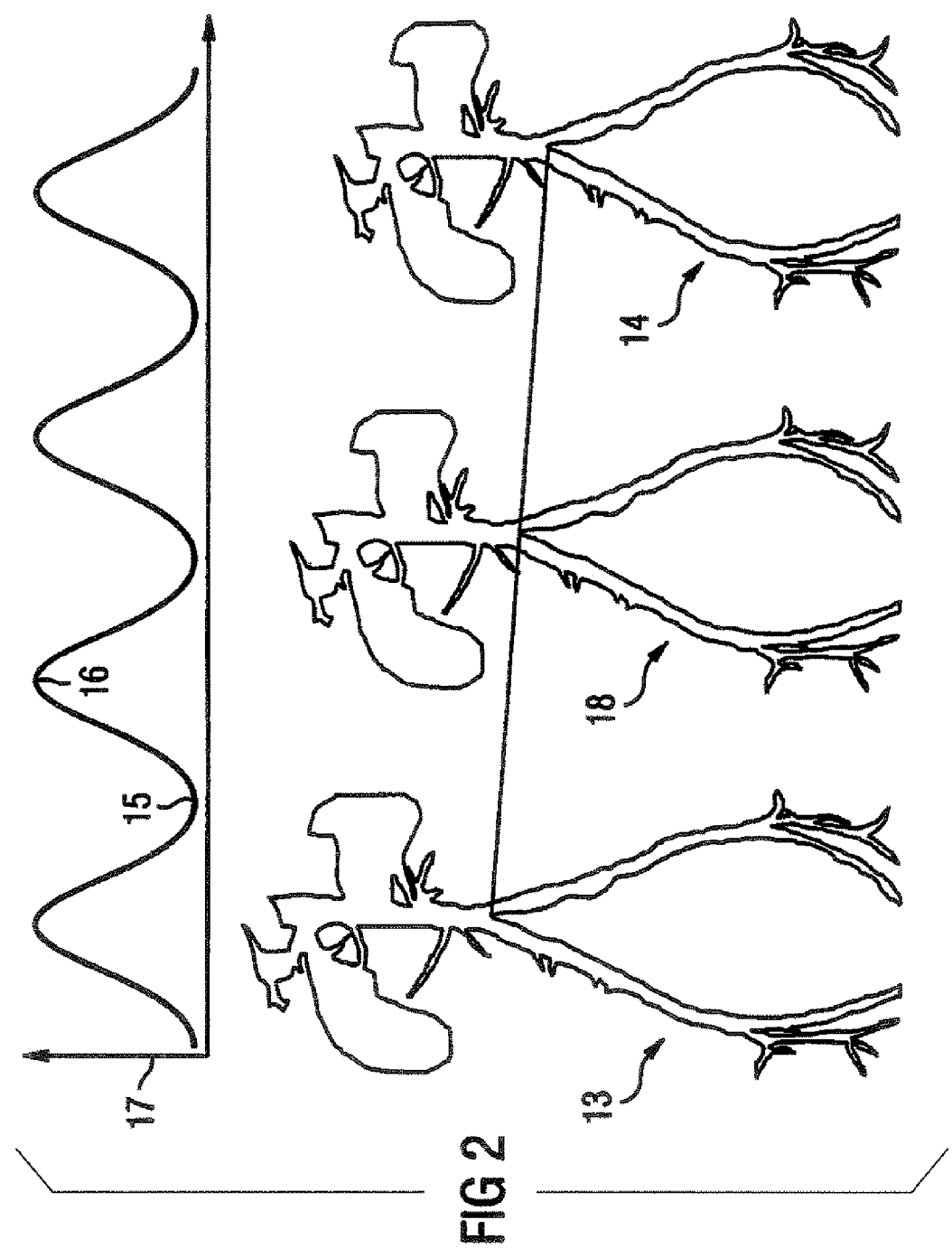

MAGNETIC RESONANCE TOMOGRAPHY METHOD AND APPARATUS WITH MOTION CORRECTION

BACKGROUND OF THE INVENTION

1. Field of the Invention

The present invention is directed to a magnetic resonance tomography apparatus of the type having a device for motion correction and to a method for motion correction in a magnetic resonance exposure in an angiography procedure with magnetic resonance-monitored vessel intervention. In particular, the present invention is directed to a magnetic resonance tomography apparatus and method wherein, an angiography procedure, a medical intervention device can be introduced into the vessel system and monitored with by magnetic resonance as to its location within the vessel system, and to thereby corrects for movements of the patient such as respiratory motion.

2. Description of the Prior Art

As a medical diagnostic modality, nuclear magnetic resonance tomography has also proven well-suited in order to implement an angiography procedure, a registration of a vessel system, and, in particular, to monitor the introduction of a medical examination device such as, for example, a catheter into a blood vessel. It is distinguished by an especially high contrast resolution for soft tissue and, in particular, allows fluids such as blood and other body fluids to be clearly distinguished relative to other tissue. Good registration of a vessel system thus is possible. The good presentation a vessel system that is already established can be further improved by introducing a contrast agent into the vessel system before the exposure (contrast agent-supported MR angiography [ceMRA]). Registration of the vessels or of the vessel tree of a specific region presented in an overview is referred to as "road map".

U.S. Pat. No. 5,792,056 discloses a magnetic resonance tomography apparatus with which an angiography procedure is implemented. A vessel intervention occurs by means of an infusion device which administers a contrast agent into the subject to be examined. As a result, a contrast-supported registration of the vessel-system is generated.

Similar to conventional angiography with other examination methods such as directed x-ray exposure or CT, an overview exposure, a road map, is initially also produced in the case of nuclear magnetic resonance tomography, to register the vessel tree that is then graphically presented. The medical examination (intervention) device is then imaged onto the road map, this being introduced into the vessel. The medical examination device is usually a guide wire with a catheter. The two exposures are subsequently overlaid on one another. The problem can occur that the first exposure, the road map, no longer corresponds to the current condition and position of the vessel system, since modifications and distortions of the vessel system occur both due to gross movements on the part of the patient but primarily due to respiratory motion. It can then no longer be reliable whether the medical examination device is still located within a vessel or whether the vessel wall has been perforated, since the catheter and/or guide wire at least sporadically produce the impression in the superimposed exposure that they are located outside the vessel tree. Such a perforation of the vessel wall is a complication that is definitely possible and must be taken very seriously in an interventional vessel operation. It is therefore desirable to avoid such a misrepresentation. The described problem occurs not only when probing or catheterizing smaller vessels wherein the vessel diameter lies on the order of magnitude of the medical intervention device (for example, catheter or guide wire) but also occurs in interventions in larger vessels, since the medical intervention devices do not necessarily lie in the center of the vessel cross-section, but have the tendency to conform to the vessel wall and to be guided thereby when advanced farther into the vessel. The movements of the vessel system can arise from a large variety of sources, such as peristaltics of the intestines and respiration. The latter leads to considerable movements of the vessel system in the region of thorax and parts of the abdomen.

U.S. Pat. No. 5,427,101 discloses a method for correcting image errors that have occurred due to motion (for example due to respiration or heart motion) of the subject being examined. In order to correct these image errors, images that belong to different motion segments are iteratively replaced by new images from which the motion has been calculated out with an algorithm (for example DVA—diminishing variance algorithm).

SUMMARY OF THE INVENTION

It is an object of the present invention to provide a magnetic resonance tomography apparatus and a method for the implementation of magnetic resonance tomography which allow a motion correction of the vessel image to be implemented in an angiography procedure with magnetic resonance-monitored vessel intervention, and to make an image available of the medical intervention device that corresponds to the true position with reference to the vessel system.

A further object of the present invention is to provide such a method and apparatus which avoid the simulation of a perforation of a vessel wall by the medical intervention device, as can occur given the superimposition of the current position of the medical intervention device with an overview registration of the vessels that was acquired at a different point in time and motion-corrected.

These objects are achieved in an inventive nuclear magnetic resonance tomography apparatus having a device for motion correction in an angiography with magnetic resonance-monitored vessel intervention with a registration unit that registers a contrast agent-supported exposure of the vessel system. This exposure ensues at the end of an expiration phase, consequently given complete exhalation of the patient, and a further exposure ensues at the end of the inspiration phase, corresponding to complete inhalation. The currently most meaningful method for acquiring a vessel tree (road map) ensues using a fast imaging sequence that allows all data for a subsequent, three-dimensional reconstruction, with a subsequent two-dimensional projection to be measured in the time span of breath being held. This method employs a T1-shortening contrast agent that is intravenously administered with an injection syringe seconds before the data acquisition, and by selecting a coincidence of the measurement time window with the contrast agent bolus dwell time in the desired target volume. The registration unit also registers a magnetic resonance-visible medical intervention device introduced into the vessel system. As a result of the motion correction, a corrected road map of the vessel system is interpolated from the exposures at end of inspiration and end of expiration, and the exposure of the intervention device is superimposed on the corrected road map. the exposures at end of inspiration and end of expiration, and the exposure of the intervention device is superimposed on the corrected road map.

The attending physician thus can recognize the position of the tip of the catheter relative to the vessel system in the image presentation during an angiography procedure with vessel intervention. Despite the moving vessel system, the catheter does not apparently periodically exceed the vessel walls. A complication wherein a vessel wall is truly perforated can now be recognized with far greater probability than in the prior art techniques.

In an embodiment, the motion sequence of the respiration can be acquired and the current position of the corrected road map be identified using a respiratory belt is applied to the patient. Such a respiratory belt is, for example, as an elastic belt that is placed around the patient which contains a wire strain gauge that acquires the magnitude of expansion and emits this as electrical measured value.

Using a technique already known in the framework of other medical examinations, the respiratory motion of the patient can be advantageously acquired in a simple and dependable way, both with respect to its momentary position and its maximum expanse and motion.

In a further embodiment, the motion sequence of the respiration can be by the excitation of a so-called navigator rod acquired perpendicular to the diaphragm or midriff, and the movements are calculated by the movement of this navigator rod that, in contrast to the entire body or vessel system, can be quickly acquired by nuclear magnetic resonance tomography.

It is thus possible to acquire the coarse of respiration of the patient without further auxiliary devices at the patient.

The motion correction device can linearly interpolate the course of respiration and the modification of the road map resulting therefrom between the registration of the end of inspiration and the registration of the end of expiration or can interpolate this course weighted with the motion sequence of the respiration.

As a result of the linear interpolation, it is possible to achieve an adaptation of the road map that is adequately precise for many applications and that can be simultaneously realized with little calculating outlay. A more precise interpolation may be needed, for example if the vessel diameters are small and even slight movements of a catheter that has a diameter on the order of magnitude of this vessel diameter lead to an apparent puncture of the vessel wall. If so, an adaptation of the road map can ensue by a somewhat more involved, weighted interpolation between the two limit conditions of end of inspiration and end of expiration, i.e. by weighting with the motion curve of the respiration.

In a nuclear magnetic resonance tomography apparatus having a device for motion correction as described above, a contrast agent-supported registration of the vessel system in an angiography procedure is undertaken with magnetic resonance-monitored vessel intervention. Further, the magnetic resonance-visible medical intervention device introduced into the vessel system also is registered. The device for motion correction registers a limited vessel section as follow-up section. The registration of the vessel system, (road map), is corrected according to the motion of this follow-up section and is superimposed with the registration of the medical intervention device.

With such an apparatus a fluid and a small, narrowly bounded section can be acquired well and quickly in magnetic resonance tomography. As a result, it is possible to reconstruct the motion of the entire vessel system from the motion of this small section. Particularly when a number of such sections are defined, the motion of the vessel system can be identified relatively precisely. Thus, an attending physician can implement an angiography examination with vessel interventions with magnetic resonance tomography just with the previously described magnetic resonance tomography and can monitor the exact position of a catheter.

The follow-up section can be selected by a selective slice excitation perpendicular to a larger vessel.

Such a slice excitation perpendicular to a larger vessel such as, for example, the aorta descendens, arteria iliaca communis, or the arteria renalis can be easily accomplished with known methods of magnetic resonance tomography. In particular, the acquisition of such a follow-up section, since it need ensue only with less detail and less highly resolved and is only intended to acquire the motion sequence, can ensue very quickly. It can thus also easily track the motion.

The follow-up section can be composed of the vessel section wherein the end segment of the introduced medical intervention device is located and, in particular, a correction can only ensue when this end segment of the medical intervention device is apparently no longer located within the vessel.

As a result, it is possible for the correction of the road map to be precise and exact in the vessel section that is particularly important for the medical diagnostic in the present treatment method. Because a correction only ensues when the intervention device, i.e. particularly a catheter, has apparently penetrated a vessel wall, a check can be made within the magnetic resonance tomography apparatus with little calculating outlay and expense to determine whether this has truly occurred. Further, the vessel section wherein the end of the catheter is located can be detected and found especially well, since a striking contrast in the image can be located with the end of the catheter and it is consequently only necessary to undertake a further registration of the tissue and of the liquids in the region around this end segment.

In a method for motion correction in an angiography procedure with magnetic resonance-monitored vessel intervention according to the invention, the vessel system is registered as a road map in a first step supported by contrast agent, with one registration ensuing at the end of inspiration and one registration ensuing at the end of expiration. A corrected road map is then formed by interpolation of a road map from the registration in the end of inspiration and from the registration in the end of expiration and subsequent adaptation to the current position of the respiratory motion of the patient. A magnetic resonance-visible medical intervention device introduced into the vessel system is then registered, and the corrected road map as well as the registration of the intervention device are imaged on top of one another.

The inventive method has the advantages that have already been described for the magnetic resonance tomography apparatus described above.

The acquisition of the motion course of the respiration can ensue using a respiration belt or with a navigator rod.

The interpolation of the road map between the registrations in the end of inspiration of the end of expiration can ensue by means of a linear or a weighted interpolation.

In the inventive method for motion correction in an angiography examination with magnetic resonance-monitored vessel intervention, the vessel system is registered contrast agent-supported as a road map in a first step, and a corrected road map is then formed on the basis of the motion of at least one vessel section that is referred to as follow-up section. This follow-up section is identified by means of a time method of flight or a phase contrast method. The road map is then adapted to the motion of this follow-up section, and a magnetic resonance-visible, medical intervention device introduced into the vessel system is registered in a further step and this image together with the image of the road map are presented on top of one another.

This alternative method of the invention also exhibits the advantageous that have already been described.

A selective slice excitation perpendicular to larger vessels can be employed as the follow-up section.

That vessel section wherein an end segment of the intervention device is located also can serve as the follow-up section, and a correction of the road map can then only ensue when this end segment of the intervention device is apparently no longer located within the vessel.

DESCRIPTION OF THE DRAWINGS

FIG. 1 is a schematic block diagram of a magnetic resonance tomography apparatus operable in accordance with the invention.

FIG. 2 schematically illustrates the formation of a corrected road map in accordance with the invention.

DESCRIPTION OF THE PREFERRED EMBODIMENTS

In a schematic illustration, FIG. 1 shows the structure of a magnetic resonance tomography apparatus that corresponds to the structure of a conventional magnetic resonance tomography apparatus but is operable according to the invention. A basic field magnet 1 generates a strong, optimally uniformly magnetic field for polarization of the nuclear spins in an examination region in the inside of the basic field magnet 1. The high uniformity of the basic magnet field required for a magnetic resonance measurement is mainly defined in a spherical measurement volume M. On a movable supporting table 5, a person can be introduced into the inside of the basic field magnet 1 so that the region of the human body that is to be examined is located in the inside of the measurement volume M. For correcting time-invariable influences, shim plates of ferromagnetic material are attached to suitable locations in addition to the basic field magnet 1. Further, a correction for time-variable influences and variations of the magnetic field is possible on the basis of shim coils 2. A cylindrical gradient coil system 3 is introduced into the basic field magnet 1 and is composed of three partial windings (sub-coil). Each partial winding is supplied with current by an amplifier 8 for generating a linear gradient field in the respective directions of the Cartesian coordinate system. The first partial winding of the gradient field system 3 generates a first gradient $G_x$ in the x-direction, the second partial winding generates a gradient $G_y$ in the y-direction; and the third partial winding generates a gradient $G_z$ in the z-direction. The gradient fields make it possible to select the volume to be measured and to obtain a location information by phase position and frequency of the nuclear magnetic resonance signal.

A radio-frequency antenna, which converts the radio-frequency pulses emitted by a radio-frequency power amplifier 9 via a transmission/reception diplexer 6 into an alternating magnetic field for exciting the nuclei and alignment of the nuclear spins of the subject to be examined, or the region of the subject to be examined, is arranged within the gradient field system 3. The radio-frequency antenna 4 also converts the alternating field emanating from the precessing nuclear spins, i.e. the nuclear magnetic resonance signals produced pulse sequence having one or more radio-frequency pulses and one or more gradient pulses, into a voltage that is supplied to a radio-frequency system 10 via the transmission/reception diplexer 6 and an amplifier 7.

The execution of the individual measuring sequences is controlled by a control computer 11 and an image is generated from the acquired measured data in this control computer 11. The administration of the image data and of the registration parameters needed for the execution of the individual measurements also ensue in the control computer 11. The evaluation of the image data according to various points of view also ensues in the control computer 11. In addition to a unit 19 for registering individual measured data and images, the inventive motion correction unit 20 for a road map registration also is located in this control computer 11. The corrected road map as well as an exposure of a medical intervention device are then optically displayed to the user at a terminal 12 that has a keyboard as well as one or more picture screens.

In a simplified and highly schematic fashion, FIG. 2 shows a motion correction of a road map image 18. The scanning components of the above-described magnetic resonance tomography apparatus first registers an exposure of a part of the vessel system of a person as angiography. This ensues at an end of expiration 13 corresponding to the person completely exhaling as well as at an end of inspiration 14 corresponding to the person completely inhaling. In the example illustrated, a vessel tree of the abdominal space as well as the two kidneys having good circulation can be seen. For illustration, respiratory motion is also shown as a curve 17 which, for example, can be acquired from a respiratory belt 21. With such a respiratory belt 21, the expansion of the belt 21 due to the respiratory motion of the patient is converted into an electrical signal.

The belt 21 can be arranged in the region of the lower abdomen in order to acquire the typical respiration of the diaphragm, or directly around the rib cage in order to acquire the expansion of the rib cage during respiration. The curve 17 that is derived due to the respiratory motion and that is basically sinusoidal corresponds to the air volume that has been inhaled. A minimum 15 of the registered respiratory motion of this respiratory belt therefore corresponds to the registration at the end of expiration 13, and a minimum 16 of the periodic function corresponds to a registration in the end of inspiration 14.

The acquisition of the motion of the respiration, alternatively, can ensue by exciting nuclear spins in and obtaining magnetic resonance signals from a narrow, rod-shaped section of the body or rib cage, referred to as a navigator rod, essentially perpendicular to the diaphragm. Signals representing this navigator rod are obtained by the magnetic resonance tomography apparatus itself, and the variation and motion of this rod is acquired, as expansions, elongations and shifts. Since this is only a matter of a small, limited volume, this can be measured quickly and with the necessary speed in order to acquire the motion.

When an angiography exposure is now to be made wherein a medical intervention device is to be introduced into the vessel system, for example a catheter, then the two exposures presented here are initially registered as static exposures. The patient, accordingly, is asked to hold his or her breath once having maximally exhaled and a second time having maximally inhaled. An exposure ensues in both conditions. The respiratory motion is then acquired via the above-described methods, i.e. via a respiratory belt 21 as an example. A synchronization with the point of the motion that is current at the moment ensues by means of the respiratory belt 21. The interpolation between the two limit images can then simply ensue linearly or according to some other suitable function. This is indicated by a straight line in the schematic illustration of FIG. 2, proceeding from the exposure at the end of expiration 13 via the corrected road map 18 that corresponds to the current condition of the vessel tree to the exposure at end of inspiration 14. It presents the modification of a point in the vessel tree that is correspondingly readjusted by means of the respiratory motion. For better illustration, this motion is shown in a sequence from left to right over time. If, corresponding to reality, the exposures were shown on top of one another here, this point would move by only a very small distance essentially perpendicularly from top to bottom. Each point of the exposure at end of expiration 13, accordingly, is thus linearly shifted over a time period of the above-described respiratory motion 17 to its corresponding point in the exposure at end of inspiration 14 constantly over time and is then shifted back.

When the corrected road map 18 is then synchronized and produced in this way, the illustrated position of the intervention device in the MR road map outside the vessel tree given an introduced medical intervention device (for example a guide wire, measurement catheter, balloon catheter or stent catheter) is highly likely not an artifact-caused illusion but the representation of a serious complication of having punctured the vessel wall with the medical intervention device. By reducing the probability that the illustration of the medical intervention device lying outside the vessel illusory, the decision latitude for the interventional radiologist is restricted and minimally invasive or vessel-surgical corrective measures can be quickly undertaken.

For smaller vessels wherein the catheter has a diameter that lies on the order of magnitude of the vessel diameter however, a linear interpolation can already lead to errors. In this case, it is possible to employ an interpolation weighted with the respiratory motion instead of a uniform displacement velocity, i.e. a linear interpolation. As can be seen from the diagram of the respiratory motion 17, this does not ensue in triangular blitz that would correspond to a linear motion but with a non-uniform curve that is somewhat reminiscent of a sine function. When the shift velocity of the individual picture elements between the two limit images of the end of expiration 13 and the end of inspiration 14 is weighted with this motion curve, the follow-up of the corrected road map 18 is more precise.

Alternatively, only a single exposure of the vessel system can form the basis here and, by acquiring a cross-section of a larger vessel, this image can be corrected in shifting fashion in two directions both magnifying as well as demagnifying or, respectively, corresponding to inspiration and expiration.

Although modifications and changes may be suggested by those skilled in the art, it is the intention of the inventor to embody within the patent warranted hereon all changes and modifications as reasonably and properly come within the scope of his contribution to the art.

I claim as my invention:

1. A magnetic resonance tomography apparatus comprising:
a magnetic resonance data acquisition system which registers a contrast agent-supported exposure of a vessel system of a subject in an angiography examination, including a first exposure at an end of expiration of said subject and a second exposure at an end of inspiration of said subject, and real time exposures of a magnetic resonance-visible medical intervention device introduced into said vessel system; and
a motion-correction unit connected to said magnetic resonance data acquisition system which interpolates a motion-corrected exposure of said vessel system from said first and second exposures and superimposes a current exposure of said medical intervention device and said motion-corrected exposure of said vessel system.

2. A magnetic resonance tomography apparatus as claimed in claim 1 further comprising a respiratory belt adapted for application to said subject for acquiring a respiratory signal from said subject, and wherein said motion-correction unit is supplied with said respiratory signal and generates a curve therefrom representing respiratory motion of said subject and determines, from said curve, a current position for said motion-corrected exposure of said vessel system.

3. A magnetic resonance tomography apparatus as claimed in claim 2 wherein said motion-correction unit generates said motion-corrected exposure of said vessel system by linear interpolation between a time of said first exposure, determined from said curve, and a time of said second exposure, determined from said curve.

4. A magnetic resonance tomography apparatus as claimed in claim 2 wherein said motion-correction unit generates said motion-corrected exposure of said vessel system by interpolating between a time of said first exposure, determined from said curve, and a time of said second exposure, determined by said curve, weighted according to said curve.

5. A magnetic resonance tomography apparatus as claimed in claim 1 wherein said magnetic resonance data acquisition system acquires magnetic resonance signals from a navigator rod substantially perpendicularly intersecting a diaphragm of said subject, and wherein said motion-correction unit generates a curve from said magnetic resonance signals from said navigator rod representing respiratory motion of said subject, and determines a current position for said motion-corrected exposure of said vessel system along said curve.

6. A magnetic resonance tomography apparatus as claimed in claim 5 wherein said motion-correction unit generates said motion-corrected exposure of said vessel system by linear interpolation between a time of said first exposure, determined from said curve, and a time of said second exposure, determined from said curve.

7. A magnetic resonance tomography apparatus as claimed in claim 5 wherein said motion-correction unit generates said motion-corrected exposure of said vessel system by interpolating between a time of said first exposure, determined from said curve, and a time of said second exposure, determined by said curve, weighted according to said curve.

8. A magnetic resonance tomography apparatus comprising:
a magnetic resonance data acquisition system which registers a contrast agent-supported exposure of a vessel system of a subject including a first exposure at an end of expiration of said subject and a second exposure at an end of inspiration of said subject, and an exposure of a magnetic resonance-visible medical intervention device introduced into said vessel system; and
a motion-correction unit connected to said magnetic resonance data acquisition system which identifies at least one vessel section as a follow-up section from at least one of said first and second exposures, and generates a motion-corrected exposure of said vessel system based on motion of said follow-up section, and superimposes said motion-corrected exposure of said vessel system with a current exposure of said intervention device.

9. A magnetic resonance tomography apparatus as claimed in claim 8 wherein said motion-correction unit identifies said follow-up section using a time of flight method.

10. A magnetic resonance tomography apparatus as claimed in claim 8 wherein said motion-correction unit identifies said follow-up section using a phase contrast method.

11. A magnetic resonance tomography apparatus as claimed in claim 8 wherein said motion-correction unit identifies said follow-up section by a selective slice excitation perpendicular to larger vessels in said subject.

12. A magnetic resonance tomography apparatus as claimed in claim 8 wherein said motion-correction unit identifies a vessel section, as said follow-up section, in which an end segment of said intervention device introduced into said subject is situated.

13. A magnetic resonance tomography apparatus as claimed in claim 12 wherein said motion-correction unit generates said motion-corrected exposure of said vessel system only if said end segment of said intervention device is not located within a vessel in said vessel system.

14. A magnetic resonance tomography method comprising the steps of:
conducting an angiography examination of a subject, with a magnetic resonance data acquisition system which registers a contrast agent-supported exposure of a vessel system of said subject, including obtaining a first exposure at an end of expiration of said subject and obtaining a second exposure at an end of inspiration of said subject, and obtaining real-time exposures of a magnetic resonance-visible medical intervention device introduced into said vessel system; and
correcting for motion of said subject during said angiography examination by interpolating a motion-corrected exposure of said vessel system from said first and second exposures and superimposing a current exposure of said medical intervention device and said motion-corrected exposure of said vessel system.

15. A method as claimed in claim 14 further comprising applying a respiratory belt to said subject and acquiring a respiratory signal from said subject therewith, and generating a curve from said respiratory signal and representing respiratory motion of said subject and determining, from said curve, a current position for said motion-corrected exposure of said vessel system.

16. A method as claimed in claim 15 comprising generating said motion-corrected exposure of said vessel system by linear interpolation between a time of said first exposure, determined from said curve, and a time of said second exposure, determined from said curve.

17. A method as claimed in claim 15 comprising generating said motion-corrected exposure of said vessel system by interpolating between a time of said first exposure, determined from said curve, and a time of said second exposure, determined by said curve, weighted according to said curve.

18. A method as claimed in claim 14 comprising acquiring, with said magnetic resonance data acquisition system, magnetic resonance signals from a navigator rod substantially perpendicularly intersecting a diaphragm of said subject, and generating a curve from said magnetic resonance signals from said navigator rod representing respiratory motion of said subject, and determining a current position for said motion-corrected exposure of said vessel system along said curve.

19. A method as claimed in claim 18 comprising generating said motion-corrected exposure of said vessel system by linear interpolation between a time of said first exposure, determined from said curve, and a time of said second exposure, determined from said curve.

20. A method as claimed in claim 18 comprising generating said motion-corrected exposure of said vessel system by interpolating between a time of said first exposure, determined from said curve, and a time of said second exposure, determined by said curve, weighted according to said curve.

21. A magnetic resonance tomography method comprising the steps of:
conducting an angiography examination of a subject with a magnetic resonance data acquisition system which registers a contrast agent-supported exposure of a vessel system of said subject, including obtaining a first exposure at an end of expiration of said subject and obtaining a second exposure at an end of inspiration of said subject, and obtaining real-time exposures of a magnetic resonance-visible medical intervention device introduced into said vessel system; and
correcting for motion of said subject during said angiography examination by identifying at least one vessel section as a follow-up section from at least one of said first and second exposures, and generating a motion-corrected exposure of said vessel system based on motion of said follow-up section, and superimposing said motion-corrected exposure of said vessel system and a current exposure of said intervention device.

22. A method as claimed in claim 21 comprising identifying said follow-up section using a time of flight method.

23. A method as claimed in claim 21 comprising identifying said follow-up section using a phase contrast method.

24. A method as claimed in claim 21 comprising identifying said follow-up section by a selective slice excitation perpendicular to larger vessels in said subject.

25. A method as claimed in claim 21 comprising identifying a vessel section, as said follow-up section, in which an end segment of said intervention device introduced into said subject is situated.

26. A method as claimed in claim 25 comprising generating said motion-corrected exposure of said vessel system only if said end segment of said intervention device is not located within a vessel in said vessel system.

* * * * *